United States Patent
Durkin et al.

(10) Patent No.: US 7,425,655 B2
(45) Date of Patent: Sep. 16, 2008

(54) MONO DI & TRI CYCLIC COMPOUNDS USEFUL FOR LOWERING IGE CONCENTRATIONS

(75) Inventors: Helen G. Durkin, Manhasset, NY (US); Martin H. Bluth, West Hempstead, NY (US); Tamar A. Smith-Norowitz, Brooklyn, NY (US); Rauno Joks, Port Washington, NY (US); Alexander Kiselyov, San Diego, CA (US)

(73) Assignee: The Research Foundation of State University of New York, Albany, NY (US)

( * ) Notice: Subject to any disclaimer, the term of this patent is extended or adjusted under 35 U.S.C. 154(b) by 40 days.

(21) Appl. No.: 10/544,814

(22) PCT Filed: Feb. 9, 2004

(86) PCT No.: PCT/US2004/003686

§ 371 (c)(1),
(2), (4) Date: Apr. 7, 2006

(87) PCT Pub. No.: WO2004/071434

PCT Pub. Date: Aug. 26, 2004

(65) Prior Publication Data

US 2006/0235081 A1    Oct. 19, 2006

(51) Int. Cl.
*C07C 49/04* (2006.01)
*A01N 35/00* (2006.01)
(52) U.S. Cl. .................... 568/415; 514/688
(58) Field of Classification Search ............... 568/415; 514/688

See application file for complete search history.

(56) References Cited

OTHER PUBLICATIONS

Santi et al., Roger-P32 metabolism in sugar and fodder beets, Montecatini, Ist. Ric. Agrar. (1962) 22 PP.*

* cited by examiner

*Primary Examiner*—Jafar Parsa
(74) *Attorney, Agent, or Firm*—Scully, Scott, Murphy & Presser, P.C.

(57) ABSTRACT

The present invention is directed novel compounds which are derivatives of minocycline or doxycycline, pharmaceutical compositions containing same and use thereof in lowering excess IgE levels in a mammal suffering from a disease where IgE is pathogenic.

6 Claims, No Drawings

MONO DI & TRI CYCLIC COMPOUNDS USEFUL FOR LOWERING IGE CONCENTRATIONS

BACKGROUND OF THE INVENTION

This invention relates to novel derivatives of minocycline and doxycline, pharmaceutical compositions containing same and their use in lowering IgE levels in mammals, especially humans, suffering from a disease where IgE is pathogenic, such as allergies, asthma, especially human allergic response, and diseases associated with an inflammatory response.

Diseases involving inflammation are characterized by the influx of certain cell types and mediators, the presence of which can lead to tissue damage and sometimes death. Diseases involving inflammation are particularly harmful when they afflict the respiratory system, resulting in obstructed breathing, hypoxemia, hypercapnia and lung tissue damage. Obstructive diseases of the airways are characterized by air flow limitation (i.e., airflow obstruction or narrowing) due to constriction of airway smooth muscle, edema and hypersecretion of mucous leading to increased work in breathing, dyspnea, hypoxemia and hypercapnia.

A variety of inflammatory agents can provide air flow limitation, such as for example, allergens. In particular, allergens and other agents in allergic or sensitized animals (i.e., antigens and haptens) cause the release of inflammatory mediators that recruit cells involved in inflammation. Such cells include lymphocytes, eosinophils, mast cells, basophils, neutrophils, macrophages, monocytes, fibroblasts and platelets. A variety of studies have linked the degree, severity and timing of the inflammatory process with the degree of airway hyperresponsiveness. Thus, a common consequence of inflammation is airflow limitation and/or airway hyperresponsiveness.

Asthma is a significant disease of the lung which is typically characterized by periodic air flow limitation and/or hyperresponsiveness to various stimuli which results in excessive airways narrowing. Other characteristics can include inflammation of airways and eosinophila. More particularly, allergic asthma is often characterized by eosinophilic airway inflammation and airway responsiveness.

An estimated 16 million persons in the U.S. have asthma, which is about 10% of the population. The numbers have increased about 25% in the last 20 years. The estimated cost of treating asthma in the U.S. exceeds $6 billion. About 25% of patients with asthma who seek emergency care require hospitalization. The largest single direct medical expenditure for asthma has been in patient hospital services (emergency care), at a cost of greater than $1.6 billion. The cost for prescription medications is at least $1.1 billion.

According to the National Ambulatory Medical Care Survey, asthma accounts for 1% of all ambulatory care visits and the disease continues to be a significant cause of missed school days in children. Despite improved understanding of the disease process and better drugs, asthma morbidity and mortality continues to rise in this country and worldwide. Thus, asthma constitutes a significant public health problem.

The pathophysiologic processes that attend the onset of an asthmatic episode can be broken down into essentially two phases, both marked by bronchioconstriction, that causes wheezing, chest tightness, and dyspnea. The first, early phase asthmatic response is triggered by allergens and irritants. Allergens cross-link immunoglobulin (IgE) molecules bound to receptors on mast cells and basophils, causing them to release a number of pre-formed inflammatory mediators, including histamine. Additional triggers include the osmotic changes in airway tissues following exercise and/or the inhalation of cold, dry air. The second, late phase response that follows is characterized by infiltration of activated eosinophilis and other inflammatory cells into airway tissues, epithelial desquamation and by the presence of highly viscous mucus within the airway. The damage caused by this inflammatory response leaves the airways "primed" or sensitized, such that smaller triggers are required to elicit subsequent asthma symptoms.

For instance, human allergic asthma, a disease characterized by airway hyperresponsiveness and bronchial inflammation, is mediated by a variety of activated leukocytes, including eosinophils, mast cells, CD4+ T lymphocytes, and CD19+ B cells.

Current treatments, which improve airway hyperresponsivenss, include various anti-inflammatory agents, which reduce mucosal inflammation and asthma pathogenesis; however their efficacies vary markedly.

Short acting $\beta_2$-adrenegric agonists, terbutaline and albuterol, long the mainstay of asthma treatment, act primarily during the early phase as bronchodilators. The newer long acting $\beta_2$ agonists do not possess significant anti-inflammatory activity; they have no effect on bronchial hyperreactivity.

Numerous other drugs target specific aspects of the early or late asthmatic responses. For example, antihistamines, like loratadine, inhibit early histamine-mediated inflammatory responses. Other antihistamines, such as azelastine and ketotifen, have both anti-inflammatory and weak bronchodilatory effects, but they currently do not have any established efficacy in asthma treatment.

Phosphodiesterase inhibitors, like theophylline/xanthines, may attenuate late inflammatory responses, but there is no evidence that the compounds decrease bronchial hyperreactivity. Anticholinergics, like ipratopium bromide, which are used in cases of acute asthma to inhibit severe bronchoconstruction, have no effect on early or late phase inflammation, no effect on bronchial hyperreactivity and therefore essentially have no role in chronic therapy.

The corticosteroid drugs, like budesonide, are among the most potent anti-inflammatory agents. Inflammatory mediators or release inhibitors, like cromolyn and nedocromil, act by stabilizing mast cells and inhibiting the late phase inflammatory response to allergen. Thus, cromolyn and nedocromil, as well as the corticosteroids, all reduce bronchial hyperactivity by minimizing the sensitivity effect of inflammatory damage to the airways. These anti-inflammatory agents, however, do not produce bronchodilation.

Thus, while numerous drugs are currently available for the treatment of asthma, these compounds are primarily palliative and/or have significant side effects.

Unfortunately, none of the aforementioned drugs target the underlying cause of asthma.

Consequently, new therapeutic approaches which target the underlying cause rather than the cascade of symptoms would be highly desirable. The present inventors have searched for the underlying cause of asthmas, especially human allergic asthma. In asthma, CD4+ T cells secrete IL-4, a (Th-)2 type cytokine, which is required for IgE production and which is implicated in airway hyperresponsiveness, as well other cyctokines which increase IgE production.

The present inventors have found that a tetracycline congener, minocycline or doxycycline suppress human and murine IgE production. More specifically, it has been found that minocycline and doxycycline lower IgE concentrations. Further, it has been found that minocycline suppresses human and murine IgE production in vivo and that minocycline and another tetracycline congener, doxycycline, suppresses human IgE production in vitro.

It has been reported that allergic steroid dependent asthmatic patients treated with an oral administration of minocycline improved their symptoms (A.M. and P.M.), and decreased oral corticosteroid requirements See, Joks, et al., *J. Allergy Clin. Immunol.* 1998, 101:562. Additional studies of O'Dell, et al. in *Arthritis Rheum:* 1997, 40: 842-848 and *Arthritis Rheum:* 1999, 42:1691-1695 have shown that treatment of mild and moderate rheumatoid arthritis (RA) patients with minocycline had no side effects, and appears to be an effective therapy for early RA. Moreover, Yu, et al. in *Arthritis Rheum:* 1992, 35: 1150-1155 reported that treatment of dogs with minocycline or doxycycline reduced the severity of osteoarthritis (OA), while studies by Thong, et al. in *Clin Exp Immunol.,* 1979, 35:443-446, have shown that doxycycline and tetracycline inhibit the ability of mice to mount delayed-type hypersensitivity responses. Further, studies in vitro have demonstrated that treatment of human whole blood cultures with minocycline or tetracycline at physiological doses inhibits mitotic responses to phytohemagglutinin (See Ingham, et al., *Antimicrob Chemother,* 1991, 27: 607-617) and inhibits inducible nitric oxide synthase (iNOS) expression by murine macrophages See Amin, et al., *PNAS,* 1996, 93: 14014-14019. In addition, it has been found that both minocycline and doxycycline suppress anti-CD40 rhIL-4 mediated in vitro induction of IgE responses by patient PBMC (peripheral blood mononuclear cells) in a dose dependent manner. (Smith-Norowitz, et al. *Annals of Allergy, Asthma & Immunology,* 2002, 89:8, 172-179. In addition, it has been shown that doxycycline suppresses PHA/IL-4 mediated IgE response by normal mouse spleen cells. Kuzin, et al. *International Immunol* 12, 921-931 (2000).

Although minocycline and doxycycline show effectiveness in suppressing excess IgE levels, being tetracyclines, they have the same adverse effects associated with tetracyclines. For example, a high percentage of patients are unable to tolerate oral tetracyclines for extended periods. The intolerance to tetracyclines can manifest itself into gastrointestinal problems, e.g., epigastric pain, nausea, vomiting and diarrhea or other problems related to taking the tetracyclines for long term treatment, such as mucosal candidiasis, staining teeth and the like.

The objective of the present invention is to find molecules that suppress IgE products, and reduce and/or eliminate the aforementioned side effects associated with tetracyclines. The present invention is directed to a means of achieving this objective by making modifications of the structures of the minocycline and doxycycline. More specifically, the present invention is directed to these new molecules and their use in suppressing excess IgE levels in patients suffering from asthma, allergies, inflammatory conditions, or other diseases where IgE is pathogenic.

SUMMARY OF THE INVENTION

The present invention is directed to the following compounds which are effective in lowering excess IgE levels in plasma:

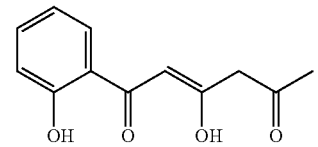

I

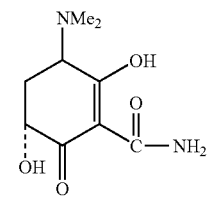

II

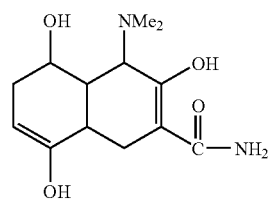

III

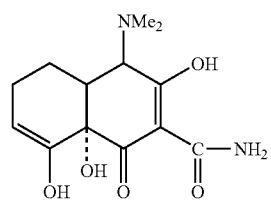

IV

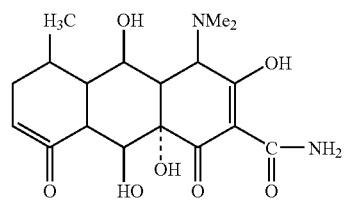

V

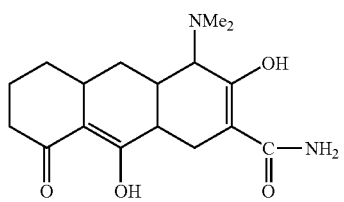

VI

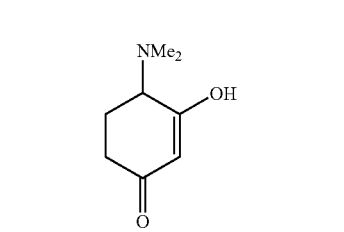

VII

-continued

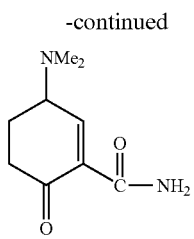

VIII and to the pharmaceutically effective salts thereof.

The present invention is also directed to pharmaceutical compositions comprising a therapeutically effective amount of a compound selected from the group consisting of Formulae I, II, III, IV, VI, VII, and VIII or pharmaceutically acceptable salts thereof and a pharmaceutical carrier thereof. In addition, the present invention is directed to a method of lowering excess IgE concentration in the plasma of a mammal comprising administering thereto a compound of Formulae I-VII or pharmaceutically acceptable salts thereof. A further embodiment is directed to treating a mammal suffering from a disease where IgE is pathogenic which method comprises administering to a mammal suffering therefrom an IgE lowering effective amount of a compound selected from the group consisting of Formulae I, II, III, IV, V, VI, VII and VIII or pharmaceutically acceptable salts thereof or combination thereof. Diseases in which the IgE is pathogenic include allergies and asthma, including human allergic asthma and inflammatory condition. In these diseases, the IgE concentration in the plasma is higher than normal. A further embodiment is directed to the prophylaxis of a mammal having an excess level of IgE in the plasma from suffering from a disease in which IgE is pathogenic which comprises administering a prophylatically effective amount of a compound of Formulae I-VIII or pharmaceutically acceptable salts thereof.

DETAILED DESCRIPTION

Each of the compounds of Formulae I-VIII and pharmaceutically acceptable salts thereof are derivatives of minocycline and doxycline. The structures of minocycline and doxycline are as follows:

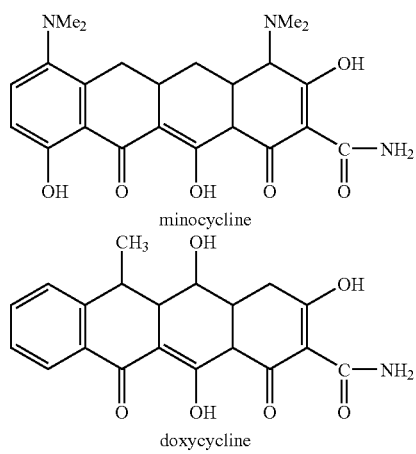

minocycline doxycycline

The inventors subjected these molecules to in silico tools to computationally analyze their molecular shapes, and as a result thereof they identified regions of overlap, which may correspond to the active sites of the molecules responsible or attributable for IgE suppression. They noted that the lower portions of the parent molecules are rich in keto-enol capabilities. Based on these calculations, they deduced the compound of Formula I, which can effect the lowering of excess IgE in the plasma.

In addition, they noted that the A ring of these tetracyclines contained a ketone, dimethyl amino and an amide group. Thus, they deduced that a structure containing just the A ring of Formula II would also lower excess IgE in the plasma. Moreover, they also deduced the structures of III and IV which are bicyclic structures containing the A & B ring of doxycycline and minocycline, respectively, having IgE suppressive activity. In addition, they deduced structures of Formula V and VI which contain the A, B &, C rings of doxycycline and minocycline, respectively, having IgE suppressive activity. Finally, they deduced structures VII and VIII, which contains the A ring without the amide at position 2 or the hydroxy groups at position 3, respectively, which also has IgE suppressive activity.

As used herein the term "patient" or "subject" refers to a warm blooded animal and preferably mammals, such as for example, cats, dogs, horse, cows, pigs, mice, rats and primate including humans. The preferred patient is humans.

Unless indicated to the contrary, the term "drug" herein is used to connote one of the aforementioned a compound which is used to lower the IgE concentration in the plasma of a mammal, e.g., human.

The compounds of the present invention that are basic in nature (Compounds II-VIII) are capable of forming a wide variety of salts with various inorganic and organic acids. The acids that may be used to prepare pharmaceutically acceptable salts.

The term "pharmaceutically acceptable salt" embraces salts commonly used to form alkali metal salt or for addition salts of free bases containing amine functionalities. The nature of the salt is not critical, provided that it is pharmaceutically acceptable. Suitable pharmaceutically acceptable acid addition salts of compounds containing amine functionalities such as present in compounds of Formulae II-VIII may be prepared from aid inorganic or organic acids. Examples of such inorganic salts are hydrochloric, hydrobromic, nitric, carbonic, sulfuric and phosphoric. Appropriate organic acid salts may be selected from aliphatic, cycloaliphatic, aromatic, araliphatic, heterocyclic, carboxylic and sulfonic classes of organic acids, examples of which include but not limited to, formic, acetic, propionic succinic, glycolic, gluconic, lactic, malic, tartaric, citric, ascorbic, glucoronic, maleic, fumaric, benzoic, methanesulfonic, benzenesulfonic, phenylacetic, stearic and the like.

Although such salts must be pharmaceutically acceptable salts for administration to a subject, e.g., mammal, it is preferably to prepare such salt from the free base (the free amine) is depicted in compounds of Formulae II-VIII by treating the same with a substantially equivalent amount of the chosen mineral or organic acid in an aqueous solvent medium or suitable organic solvent, such as methanol or ethanol. Upon evaporation of the solvent, the desired pharmaceutically acceptable salt is obtained.

Thus, as used herein when referring to the expression "one or more pharmaceutically acceptable salts thereof", it is to be understood that the term refers to "pharmaceutically acceptable salts" of compounds of Formulae II-VIII.

An embodiment of the present invention is directed to the use of IgE lowering effective amounts of a compound of Formulae I, II, III, IV, V, VI, VII or VIII or pharmaceutically acceptable salts of compounds of Formulae II-VIII or combination thereof for the suppression of elevated concentrations relative to normal concentrations of IgE in the blood plasma of a patient suffering from a disease in which IgE is pathogenic. Accordingly, compounds of Formulae I-VIII, singly or in combination, or pharmaceutically acceptable salts of the compounds of Formulae II-VIII in amounts effective in lowering the concentration of excess IgE in the plasma are useful for treating human allergic asthma. In addition, these compounds are anti-inflammatory agents and are useful, either singly or in combination to treat inflammatory conditions when administered to patients in IgE lowering effective amounts, as defined herein.

The compounds, when administered singly, are administered therefore in therapeutically effective amounts. If administered in combination, they are administered in total in therapeutically effective amounts.

The physician will determine the dosage of the compounds of Formulae I-VIII or pharmaceutically acceptable salts of compounds of Formulae II-VIII which will be most suitable and it will vary with the form of administration and the particular compound chosen, and furthermore, it will vary depending upon various factors, including but not limited to the patient under treatment, the age of the patient, the severity of the condition being treated and the like. The physician will generally wish to initiate treatment with small dosages substantially less than the optimum dose of the compound and increase the dosage by small increments until the optimum effect under the circumstances is reached. These compounds, when given orally, are administered preferably in dosages ranging from about 1 to about 400 mg/day and more preferably from about 1 to about 300 mg/day. When given parenterally, the compounds of the present invention, are administered preferably in dosages of, for example, about 1.5 to about 400 mg/day, and more preferably from about 1 to about 300 mg/day also depending upon the host and the severity of the condition being treated and the compound utilized.

This dosage regimen may be adjusted by the physician to provide the optimum therapeutic response. For example, several divided doses may be administered daily with each dose being proportionally reduced.

The compounds of Formulae I-VIII or pharmaceutically acceptable salts of compounds of Formulae II-VIII may be administered in a convenient manner, such as by oral, intravenous (where water soluble), topical, intramuscular or subcutaneous routes or by inhalation.

They may be orally administered, for example, with an inert diluent or with an assimilable edible carrier, or they may be enclosed in hard or soft shell gelatin capsules, or compressed into tablets, or incorporated directly into the food of the diet. For oral therapeutic administration, they may be incorporated with excipients and used in the form of ingestible tablets, buccal tablets, troches, capsules, elixirs, suspensions, syrups, wafers, and the like. Such compositions and preparations should contain at least 1% of the compounds of Formulae I-VIII or pharmaceutically acceptable salts of Formulae II-VIII. The percentage of the compositions and preparations may, of course, be varied and may conveniently be between about 5 to about 80% of the weight of the unit. The amount of the compound of any of Formulae I-VIII or pharmaceutically acceptable salts of Formulae II-VIII used in such therapeutic-compositions is such that a suitable dosage will be obtained. Preferred compositions or preparations according to the present invention contain between about 25 mg and about 1000 mg of a compounds of Formulae II-VIII or the pharmaceutically acceptable salts of compounds of Formulae II-VIII including those containing about 25 mg, about 50 mg, about 75 mg, about 100 mg, about 125 mg, about 150 mg, and about 300 mg.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier.

Various other materials may be present as coatings or otherwise modify the physical form of the dosage unit. For instance, tablets, pills, or capsules may be coated with shellac, sugar or both. A syrup or elixir may contain a compound of Formulae I-VIII or pharmaceutically acceptable salts of compounds of Formulae II-VIII, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, a compound of Formulae I-VIII or pharmaceutically acceptable salts of compounds of Formulae II-VIII may be incorporated into sustained-release preparations and formulations. For example, sustained release dosage forms are contemplated wherein a compound of Formulae I-VIII or pharmaceutically acceptable salts of compounds of Formulae II-VIII is bound to an ion exchange resin which, optionally, can be coated with a diffusion barrier coating to modify the release properties of the resin or wherein a compound of Formulae I-VIII or a pharmaceutically acceptable salt of compound of Formulae II-VIII is associated with a sustained release polymer known in the art, such as hydroxypropylmethylcellulose and the like.

A compound of Formulae I-VIII or pharmaceutically acceptable salts of compounds of Formulae II-VIII may also be administered parenterally. It is especially advantageous to formulate parenteral compositions in dosage unit form for ease of administration and uniformity of dosage. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersions and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating a compound of Formulae I-VIII or pharmaceutically acceptable salts of compounds of Formulae II-VIII in the required amount in the appropriate solvent with any of the other ingredients enumerated above, as required, followed by filtered sterilization. Generally, dispersions are prepared by incorporating a sterilized compound of Formulae I-VIII or pharmaceutically acceptable salts of compounds of Formulae II-VIII into a sterile vehicle which contains the basic dispersion medium and the required other ingredients from those enumerated above. In the case of sterile powders, the above solutions are vacuum dried or freeze-dried, as necessary.

A compound of Formulae I-VIII or pharmaceutically acceptable salts of compounds of Formulae II-VIII can also be formulated and administered to the patient in solid or liquid particulate form by direct administration, e.g., inhalation, into the respiratory system.

Solid or liquid particulate forms of a compound of Formulae I-VIII or pharmaceutically acceptable salts of compounds of Formulae II-VIII prepared for practicing the present invention include particles of respirable size: that is, particles of a size sufficiently small to pass through the mouth and larynx upon inhalation and into the bronchi and alveoli of the lungs. In general, particles ranging from about 1 to 10 microns in size are within the respirable range. The pharmaceutical compositions containing a compound of Formulae I-VIII or pharmaceutically acceptable salts of compounds of Formulae II-VIII are preferably administered by direct inhalation into the respiratory system for delivery as a mist or other aerosol or dry powder. Particles of non-respirable size which are included in the aerosol tend to be deposited in the throat and swallowed; thus the quantity of non-respirable particles in the aerosol is preferably minimized.

In the manufacture of the preferred local formulation, in accordance with the description herein, a compound of Formulae I-VIII or pharmaceutically acceptable salts of compounds of Formulae II-VIII are typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation.

Aerosols of liquid particles comprising a compound of Formulae I-VIII or pharmaceutically acceptable salts of compounds of Formulae II-VIII may be produced by any suitable means, such as inhalatory delivery systems. One is a traditional nebulizer which works in a mechanism similar to the familiar perfume atomizer. The airborne particles are generated by a jet of air from either a compressor or compressed gas cylinder-passing through the device (pressure driven aerosol nebulizer). In addition, newer forms utilize an ultrasonic nebulizer by vibrating the liquid at a speed of up to about 1 MHz. See, e.g., U.S. Pat. No. 4,501,729, the contents of which are incorporated by reference. Nebulizers are commercially available devices and can transform solutions or suspensions comprising a compound of Formulae I-VIII or pharmaceutically acceptable salts of compounds of Formulae II-VIII into a pharmaceutical aerosol mist either by means of acceleration of compressed gas, typically air or oxygen, through a narrow venturi orifice or by means of ultrasonic agitation. Suitable formulations for use in nebulizers consist of a compound of the Formulae I-VIII or pharmaceutically acceptable salts of compounds of Formulae II-VIII in a liquid carrier. The carrier is typically water (and most preferably sterile, pyrogen-free water) or a dilute aqueous alcoholic solution, preferably made isotonic but may be hypertonic with body fluids by the addition of, for example, sodium chloride. Optional additives include preservatives if the formulation is not made sterile, for example, methyl hydroxybenzoate, as well as antioxidants, flavoring agents, volatile oils, buffering agents and surfactants, which are normally used in the preparation of pharmaceutical compositions.

Aerosols of solid particles comprising a compound of Formulae I-VIII or pharmaceutically acceptable salts of compounds of Formulae II-VIII may likewise be produced with any solid particulate medicament aerosol generator. Aerosol generators for administering solid particulate medicaments to a subject produce particles which are respirable, as explained above, and generate a volume of aerosol containing a predetermined metered dose of a medicament at a rate suitable for human administration. One illustrative type of solid particulate aerosol generator is an insufflator. Suitable formulations for administration by insufflation include finely comminuted powders which may be delivered by means of an insufflator or taken into the nasal cavity in the manner of a snuff. In the insufflator, the powder (e.g., a metered dose thereof effective to carry out the treatments described herein) is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the compound of Formulae I-VIII or pharmaceutically acceptable salts of compounds of Formulae II-VIII or of a powder blend comprising a compound of the Formulae I-VIII or pharmaceutically acceptable salts of compounds of Formulae II-VIII a suitable powder diluent, such as lactose, and an optional surfactant. A second type of illustrative aerosol generator comprises a metered dose inhaler. Metered dose inhalers are pressurized aerosol dispensers, typically containing a suspension or solution formulation of a compound of Formulae I-VIII in a liquefied propellant. During use, these devices discharge the formulation through a valve, adapted to deliver a metered volume, from about 10 to about 22 microliters to produce a fine particle spray containing tetracycline.

Any propellant may be used in carrying out the present invention, including both chlorofluorocarbon-containing propellants and non-chlorofluorocarbon-containing propellants. Fluorocarbon aerosol propellants that may be employed in carrying out the present invention including fluorocarbon propellants in which all hydrogens are replaced with fluorine, chlorofluorocarbon propellants in which all hydrogens are replaced with chlorine and at least one fluorine, hydrogen-containing fluorocarbon propellants, and hydrogen-containing chlorofluorocarbon propellants. Examples of such propellants include, but are not limited to: $CF_3CHFCF_2$, $CF_3CH_2CF_2H$, $CF_3CHFCF_3$, $CF_3CH_2CF_3$, $CF_3CHCl$—$CF_2Cl$, $CF_3CHCl$—$CF_3$, $CF_3CHCl$—$CH_2Cl$, $CF_3CHF$—$CF_2Cl$, and the like. A stabilizer such as a fluoropolymer may optionally be included in formulations of fluorocarbon propellants, such as described in U.S. Pat. No. 5,376,359 to Johnson. The aerosol formulation may additionally contain one or more co-solvents, for example, ethanol, surfactants, such as oleic acid or sorbitan trioleate, antioxidants and suitable flavoring agents.

Compositions containing respirable dry particles of micronized compounds of any of Formulae I-VIII or pharmaceutically acceptable salts of compounds of Formulae II-VIII may be prepared by grinding the dry active compound, with e.g., a mortar and pestle or other appropriate grinding device, and then passing the micronized composition through a 400 mesh screen to break up or separate out large agglomerates.

The aerosol, whether formed from solid or liquid particles, may be produced by the aerosol generator at a rate of from about 10 to 150 liters per minute. Aerosols containing greater amounts of a compound of Formulae I-VIII or pharmaceutically acceptable salts of compounds of Formulae II-VIII may be administered more rapidly. Typically, each aerosol may be delivered to the patient for a period from about 30 seconds to about 20 minutes, with a delivery period of about 1 to 5 minutes being preferred.

The particulate composition comprising a compound of Formulae I-VIII or pharmaceutically acceptable salts of compounds of Formulae II-VIII may optionally contain a carrier which serves to facilitate the formation of an aerosol. A suitable carrier is lactose, which may be blended with the tetracycline in any suitable ratio.

The compounds of Formulae I-VIII or pharmaceutically acceptable salts of compounds of Formulae II-VIII may be formulated into a topical composition. Typically, such topical compositions are prepared as a liquid (both oil-in-water and water-in-oil, with or without emulsions), gels (both aqueous and non-aqueous), lotions, ointments, paste, powders and the like. The compounds of Formulae I-VIII or pharmaceutically acceptable salts of compounds of Formulae II-VIII are present in therapeutically effective amounts as defined herein. Preferably, the topical composition of the present invention contain from about 0.5% to about 95% by weight of compounds of Formulae I-VIII or pharmaceutically acceptable salts of compounds of Formulae II-VIII.

The topical compositions are most useful in treating dermatologic disorders or conditions arising from or caused by excess IgE in the plasma in a mammal, such as a topic dermatosis, inflammatory dermatosis, such as acne, and the like.

Cream, lotion, gel, stick, ointment, or topical solution, may be used as topical vehicles for compounds of the formula (I) in conventional formulations well known in the art, for example, as described in the standard text books of pharmaceutics and cosmetics, such as Harry's Cosmeticology published by Leonard Hill Books, Remington's Pharmaceutical Sciences published by Mack Publishing Co., and the British and US Pharmacopoeias. A standard emulsifying ointment base or glycerol or anhydrous polyethylene glycol are simple examples of suitable vehicles.

Examples of oils suitable for inclusion in a standard emulsifying ointment base include mineral oils, vegetable oils, synthetic fatty acid esters, fatty alcohols, lanolin and its derivatives.

These compositions will normally include a suitable emulsifier. The composition can range from liquid through semi-liquid to gel types according to the type of emulsion and quantity of any thickening agent which may be present. Examples of emulsifiers include polyhydric alcohol esters such as sorbitan monostearate, fatty acid esters such as glyceryl monostearate, and polyester derivatives of fatty acids or fatty alcohols.

These topical compositions as well as the other pharmaceutical compositions described hereinabove may also contain anti-oxidants and other conventional ingredients such as preservatives, humectants, perfumes and alcohol. Advantageously, a penetrating agent such as AZONE may also be included.

The compositions for topical treatment may also contain other therapeutic agents such as anti-infective and/or antiviral agents. Suitable anti-infective agents include the topically applicable antibacterial, anti-yeast, anti-fungal and anti-herpes agents.

The topical composition of the present invention can also be applied in therapeutic effective amounts through a transdermal patch using techniques known to one of ordinary skill in the art.

The compounds of any of Formulae I-VIII or pharmaceutically acceptable salts of compounds of Formulae II-VIII are administered by these various modes of administration in therapeutically effective amounts, as defined herein which amounts are determined by the physician.

The pharmaceutical compositions of the present invention are in association with a pharmaceutically acceptable carrier, and contain the ingredients, typically found in pharmaceutical compositions. For example, it may include excipients, fragrances, anti-oxidants, sunscreens, flavors, buffers, solubilizers, thickeners and the like. As used herein, "pharmaceutically acceptable carrier" includes any and all solvents, dispersion media, coatings, antibacterial and antifungal agents, isotonic and absorption delaying agents for pharmaceutical active substances well known in the art. Except insofar as any conventional media or agent is incompatible with the compounds of Formulae I-VIII or pharmaceutically acceptable salts of compounds of Formulae II-VIII their use in the therapeutic compositions is contemplated. Supplementary active ingredients can also be incorporated into the compositions.

Dosage unit form as used herein refers to physically discrete units suited as unitary dosages for the subjects to be treated; each unit containing a predetermined quantity of active material calculated to produce the desired therapeutic effect in association with the required pharmaceutical carrier.

The compounds of Formulae I-VIII or pharmaceutically acceptable salts of compounds of Formulae II-VIII are compounded for convenient and effective administration in effective amounts with a suitable pharmaceutically acceptable carrier in dosage unit form as hereinbefore described. A unit dosage, for example, contains a compound of Formulae I-VIII or pharmaceutically acceptable salts of compounds of Formulae II-VIII singly or in total in amounts ranging from about 50 mg to about 1000 mg. If placed in solution, the concentration of the compounds of Formulae I-VIII or pharmaceutically acceptable salts of compounds of Formulae I-VIII singly or in combination preferably ranges from about 10 mg/ml to about 250 mg/ml. The preferred mode of administration is oral.

Moreover in normal humans, not suffering from asthma or allergies or diseases wherein IgE is pathogenic, the administration of compounds of Formulae I-VIII or pharmaceutically acceptable salts of compounds of Formulae II-VIII does not increase the concentration of IgE in the plasma.

The compounds of each of Formulae I-VIII or pharmaceutically acceptable salts of compounds of Formulae II-VIII are useful in treating asthma. They are anti-inflammatory agents and can be used to treat inflammatory conditions.

The present inventors have found that the higher the concentration of the free IgE in the plasma in those patients suffering from a disease where IgE is pathogenic, the greater is the risk of the disease state becoming aggravated or worsening. By lowering the amount of the free IgE in the plasma of those patients, the physician will lower the risk of the disease state becoming worse or becoming exacerbated.

In another embodiment, the present invention is directed to the prophylaxis of the disease wherein IgE is pathogenic from becoming more severe, which method comprises administering to the patient a prophylatically effective amount of any of the compounds of Formulae I-VIII, or pharmaceutically acceptable salts of compounds of Formulae II-VIII individually or combination thereof. The effective amount in this embodiment is determined by the physician; usually, this amount is the same as the therapeutic effective amount, that was described hereinabove.

A compound of Formulae I-VIII or pharmaceutically acceptable salts of compounds of Formulae II-VIII can also be given to mammals suffering from asthma, or allergies or other diseases where IgE is pathogenic by administering to the patient a prophylactically effective amount of a compound of Formulae I-VIII or combination thereof. The effective amounts can be determined by the physician. The normal person has a free plasma concentration of IgE of less than about 50 IU/ml. Thus, the administration of the aforementioned compounds of Formulae I-VIII or pharmaceutically acceptable salts of compounds of Formulae II-VIII will prevent and/or retard the onset of allergy or allergic asthma and/or other disease where IgE is pathogenic when administered in effective amounts, as described herein. In addition, the administration thereof will prevent or lower the risk of persons having a free IgE concentration in the plasma increasing to the level where the person is at a substantial risk of suffering from a disease where IgE is pathogenic. Preferably, the free IgE level in the plasma, after such treatment, will remain less than about 50 IU/ml.

amount effective in eliminating or alleviating or curing the symptoms associated with a disease or malady where IgE is pathogenic and/or alleviating or curing the disease altogether.

The term "prophylatically effective amount" refers to the amount effective in preventing or reducing the likelihood of a mammal, e.g., patient from acquiring a disease in which IgE is pathogenic. It also refers to the amount effective in preventing a mammal afflicted with a disease or malady where IgE is pathogenic from worsening or becoming more severe.

As indicated herein, the prophylactive effective amounts and the therapeutically effective amounts can be determined by the physician; however, it is preferred that these amounts are the same.

As used herein, the term compounds of Formulae I-VIII refers to a single compound or combination of compounds having Formulae I-VIII.

As used herein, the singular denotes the plural and vice versa.

The compounds of the present invention can be prepared by art recognized techniques as shown hereinbelow.

Compounds of Formula I can be prepared as follows as shown in Scheme I:

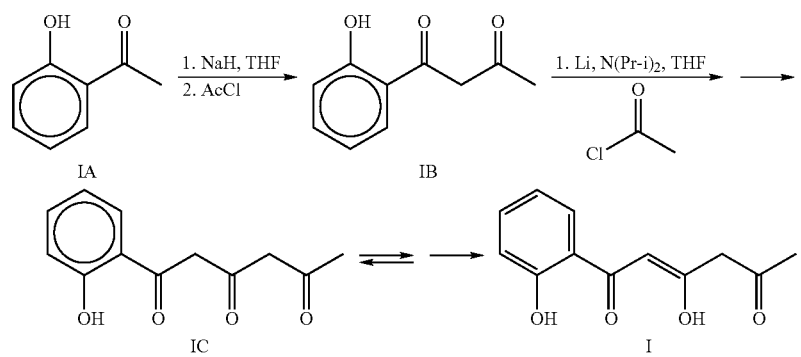

In the present specification, unless indicated to the contrary, the plural will connote the singular and vice versa.

The term "treating", "treat" or "treatment", as used herein refers to the reduction and/or alleviation of at least one adverse effect or symptom of a disease where IgE is pathogenic. It refers to the management and care of a mammalian subject, preferably humans, for the purpose of combating the disease, conditions or disorders where IgE is pathogenic, and includes the administration of any of the compounds of Formulae I-VIII, alone or in combination to delay the onset of at least one symptom or complication associated with the disease, alleviating the symptom or effect or complications associated therewith or in the alternative eliminating the disease or condition.

The term "prophylaxis" or "prevent" or synonym thereto refers to the prevention or a measurable reduction in the likelihood of a patient acquiring a disease where IgE is pathogenic, even if the mammal is suffering form another malady which debilitates it and makes it more susceptible to such a disease. If a patient or mammal is suffering from a disease where IgE is pathogenic, the term also refers to the reduction in the likelihood of the disease becoming acerbated.

The term "therapeutically effective amount" is synomous with "IgE lowering effective amounts" and refers to the For example, the phenol derivative (IA) is reacted with acetyl chloride in the presence of strong base, such as sodium amide, sodium hydride and the like in an inert solvent, such as THF under effective reacted conditions to form a compound of Formula IB. It, in turn, is reacted with acetyl chloride in the presence of a stronger base such as Li(N-i—Pr)$_2$, in an inert solvent, such as THF to form Compound IC. Compound IC enolizes to form a compound a Formula I.

Compounds of Formula II can be prepared as follows:

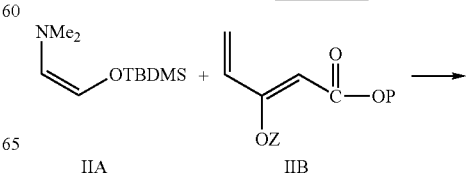

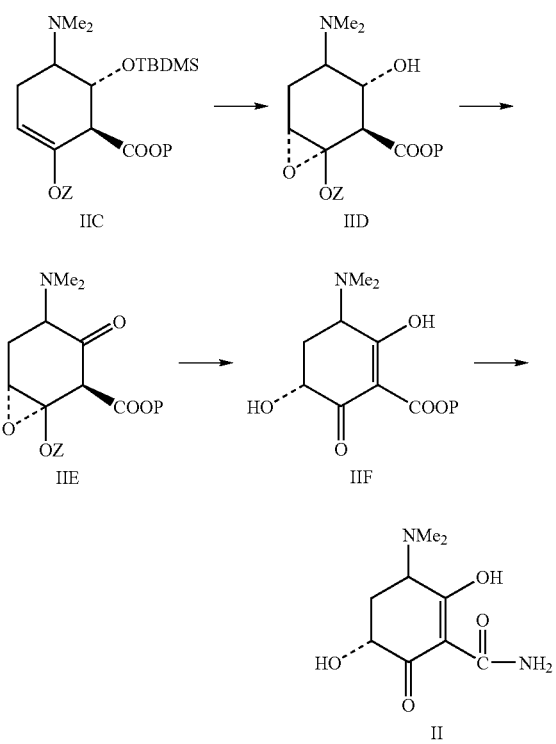

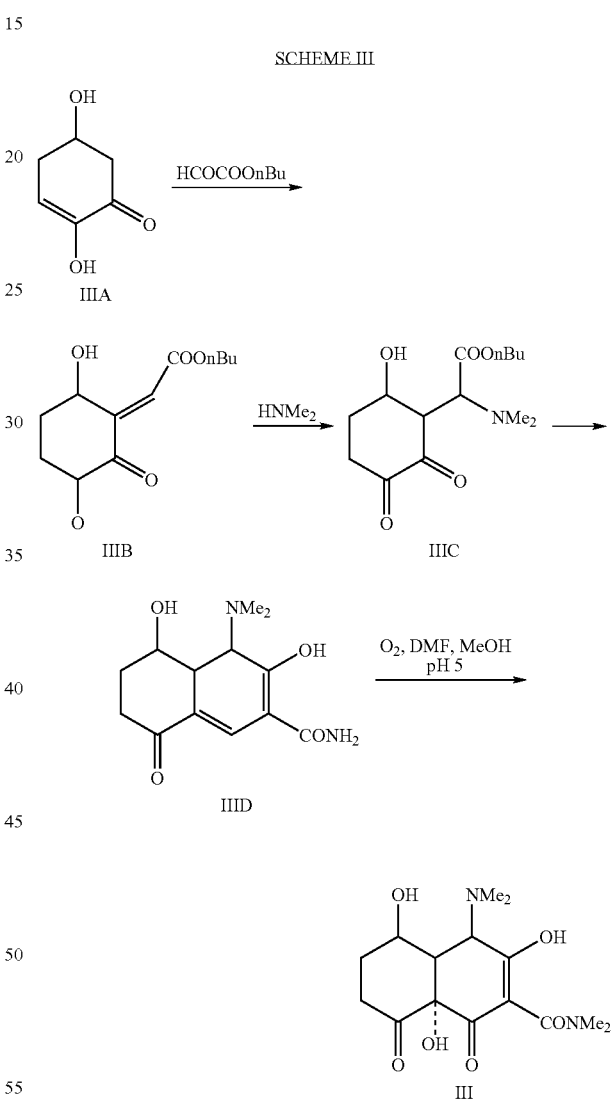

For example, the compound of Formula IIA is reacted with a diene of Formula IIB under Diels Alder reaction conditions. Preferably, the reaction is conducted in the presence of a Lewis acid catalyst, e.g., zinc halide, such as $ZnI_2$, and in an inert solvent, such as toluene, xylene, benzene and the like, and preferably xylene, under conditions sufficient to form the six membered cyclic diene IIC. The reaction may be conducted under reflux, although temperatures from about 20° C. to reflux may be used. As used hereinabove, TBDMS is t-butyl dimethylsilyl, Z is a hydroxy protecting group known in the art, and P is a chiral group, such as (+) or (−) phenylmenthyl. Various hydroxy protecting groups can be utilized, such as benzyl, carbonate and the like, and these are described on pages 10-72 of the book entitled *Protective Groups in Organic Synthesis,* by Theodora W. Greene, John Wiley & Sons, New York, N.Y., 1981, the contents of which are incorporated by reference. The cyclohexane IIC is oxidized with an oxidizing agent to form an epoxide. Preferably, the cyclohexane is reacted with m-chloroperbenzoic acid, $H_2O_2$ and the like under epoxidizing conditions sufficient to form an epoxide alcohol of Formula IID. The alcohol IID is oxidized with an oxidizing agent to form the corresponding ketone IIE. Oxidizing groups known in the art, such as $CrO_3$ or $K_2Cr_2O_7$ and the like, may be utilized as the oxidizing agent. In addition, the alcohol IID can be oxidized to IIE using oxalyl dimethyl sulfoxide in combination with one of the following reagents: acetic anhydride, $SO_3$-pyridine-triethylanine, trifluoroacetic anhydride, oxalyl chloride, tosyl chloride, chlorine, bromine, $AgB F_4$-$Et_3N$, $P_2O_5$-$Et_3N$, phenyl dichlorophosphate, trichloromethyl chloroformate, trimethylamine oxide, and the like. It is preferred that the reaction takes place using DMSO and oxalyl chloride in the presence of an amine base under Swern oxidation conditions. The epoxide IIE is oxidized to the corresponding alpha-hydroxy ketone IIF with conventional oxidizing agents such as $Br_2$, N-bromosuccinimide and the like. The Compound IIF is in equilibrium with the corresponding enol. The ester moiety of Formula IIF is reacted with ammonia to form the corresponding amide under effective amide forming conditions to form the compound of Formula II.

An exemplary procedure for preparing the compound of Formula III is as follows:

IIIA is reacted with a HCOCOOnBu and base, such as sodium hydride or sodium amide, under Claisen Condensation Reaction conditions (i.e., α-arylalkyl dealkoxy substitution reaction conditions) to form IIIB, which in turn is reacted with dimethylamine under nucleophilic reaction conditions to form IIIC. IIIC can be further converted to IIID, using the procedures described in Woodward, et al., *JACS* 84, 3222-3224, (1962) the contents of which are incorporated by reference. IIID is reacted with $O_2$ in DMF and MeOH at pH 5 to afford III.

An exemplary procedure for the preparation of Formula IV is as follows:

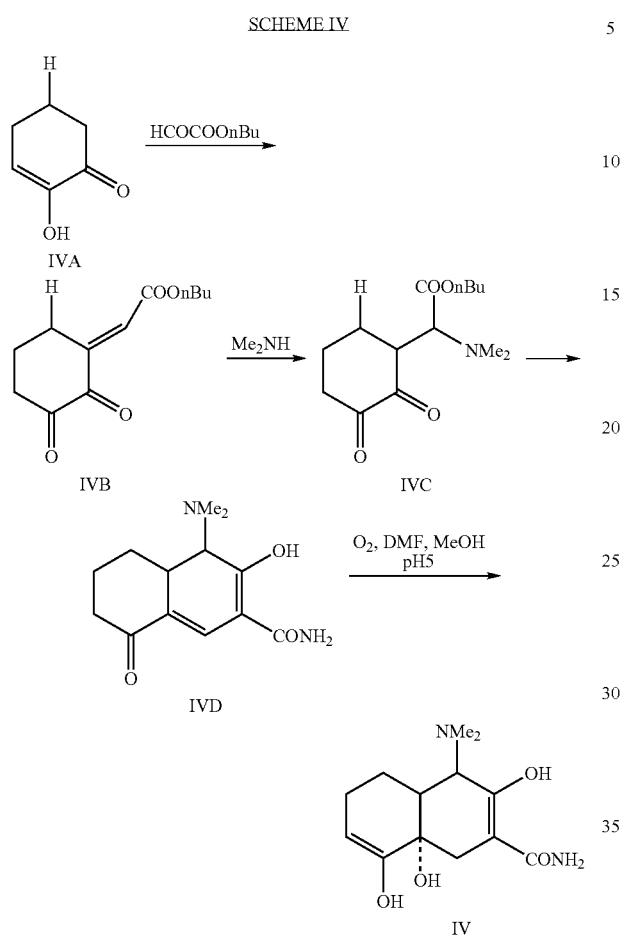

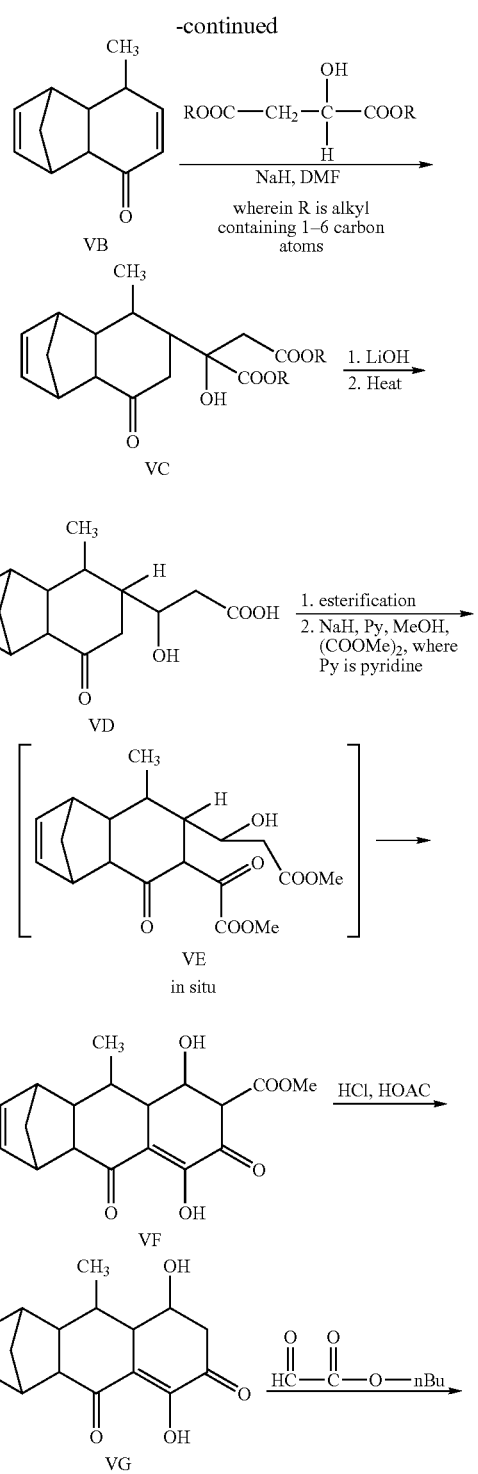

This is prepared in an analogues manner as described for preparing the compound of Formula III. The diketone, represented as its enol-ketone IVA, is reacted with HCOCOOn-Bu under Claisen Condensation conditions, (i.e., α-acylalkyldealkoxy substitution reaction conditions) to form IVB, which is reacted with dimethylamine under nucleophilic reaction conditions to form IVC. IVC is converted to IVD using the procedures described by Woodward, et al. in *JACS*, 84, 3222-3224 (1962), the contents of which are incorporated by reference to give IVD. IVD is reacted with O₂ in DMF and MeOH at pH 5 to afford IV.

An exemplary procedure of the preparation of the compound of Formula V is as follows:

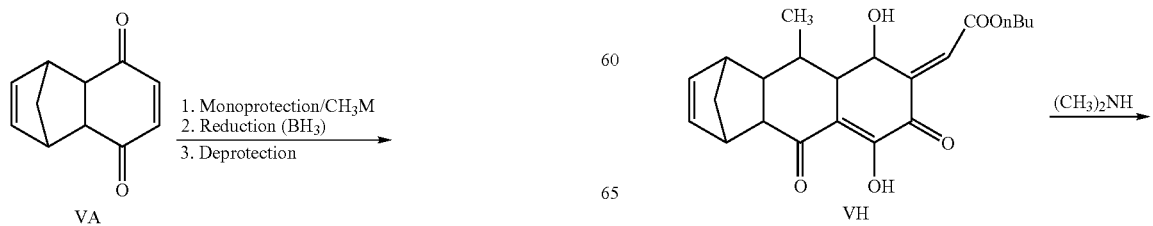

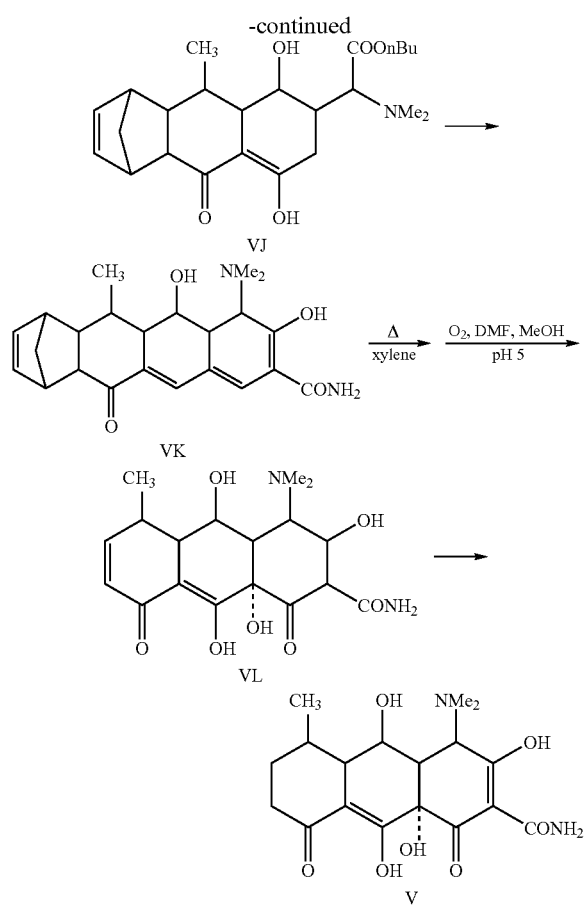

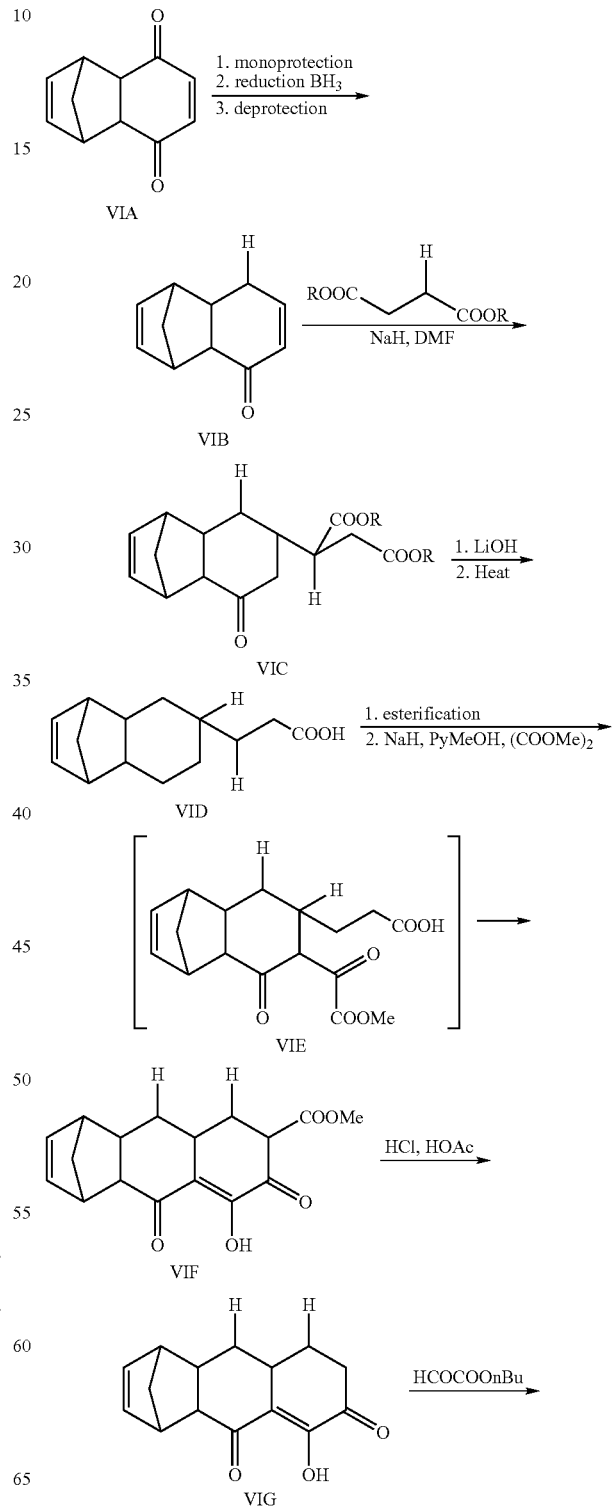

the resulting intermediate is further reacted with $O_2$ in DMF and MeOH at pH 5 to afford VL which is reduced with a reducing agent using techniques known in the art, such as by hydrogenation to form V.

Compounds of Formula VI can be prepared as follows:

One of the ketone moieties in VA is protected with protection groups known in the art, such as by reacting with ethylene glycol, MeOH in acid and the like. The non-protected ketone is reacted with an organometalic compound such as $CH_3M$, wherein M is a metal, such as lithium, e.g., $LiCH_3$ or Grignard reagent, such as $CH_3MgX$, wherein X is halide, which product is reduced in the presence of a reducing agent known in the art, boranes to reduce the resulting alcohol. The protecting group is removed to afford the ketone. VB is reacted with a succinic acid derivative, e.g., ester, such as $C_1$-$C_6$ alkyl succinate, e.g., such as methyl succinate, in the presence of base under Michael-like addition reaction conditions to form the product VC which, in the presence of base and heat decarboxylates to produce VD. VD is esterfied with alcohol such as MeOH in acid and the product thereof is reacted with methyl carbonate in base to form the product VE in situ under Claisen-like condensation reaction conditions, which in base, such as sodium hydride cyclizes under Dieckman condensation reaction conditions to form the product VF. This is in turn decarboxylates in acid and heat to form VG. In the presence of HCO COOnBu and base under Claisen condensation reaction conditions, product VH is formed, as in the preparation of Compound III. This in turn is reacted with dimethylamine under nucleophilic conditions to form the product VJ. VJ in the presence of base, such as sodium hydride and heat, such as 120° C., in DMF in accordance with the procedure described in Woodward, et al. *JACS* 84, 3222-3224 (1962), the contents of which are incorporated by reference, cyclizes to afford VK. VK is heated in xylene at a temperature sufficient to eliminate cyclopentadiene, such as from about 120° C. to 160° C., and

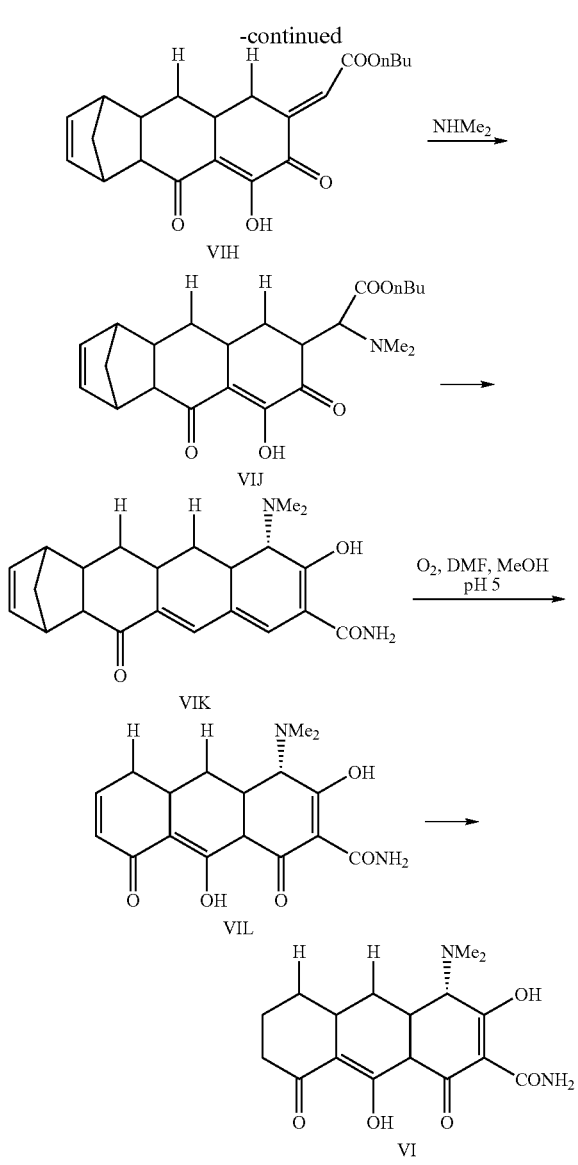

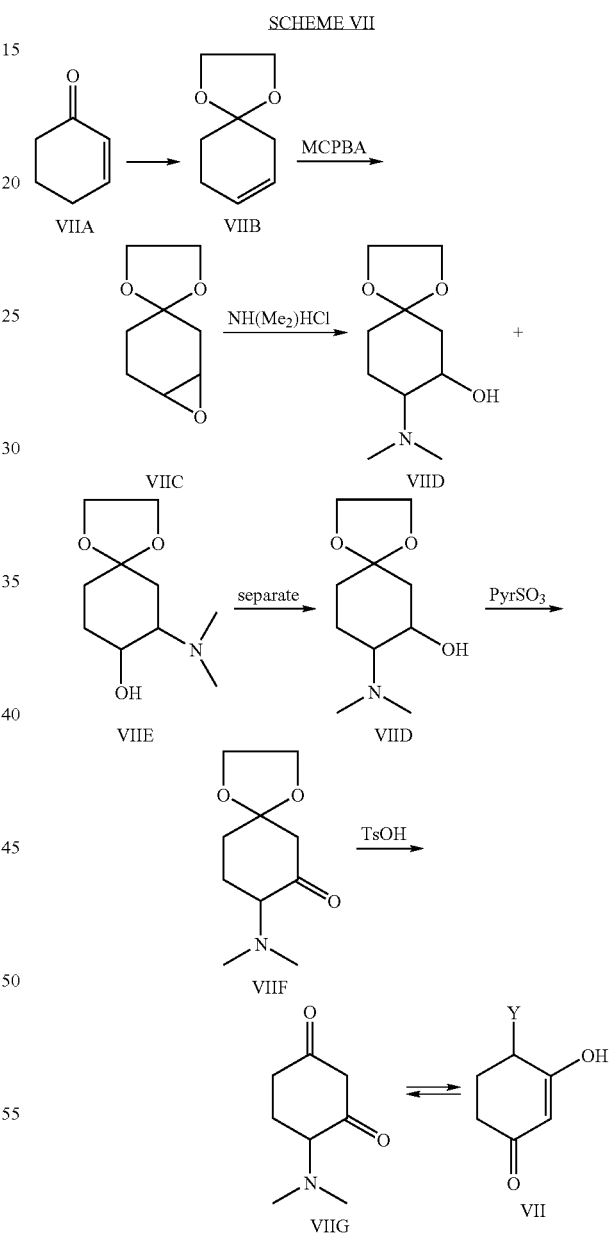

VIJ. VIJ is converted to VIK, using the procedures described in Woodward, et al. *JACS* 84, 3222-3224 (1962), the contents of which are incorporated by reference. VIK is heated in xylene under conditions sufficient to eliminate cyclopentadiene, such as from about 120° C. to about 160° C., and the resulting intermediate is reacted with $O_2$ in DMF and MeOH at pH 5 to afford VIL. A carbon-carbon double is reduced using a reducing agent by techniques known in the art, such as hydrogenation, to form VI.

Compound VII can be prepared as shown in the following scheme:

One of the ketone moieties in VIA is protected with protection groups known in the art, such as by reacting it with ethylene glycol, MeOH in acid and the like. The mono-protected ketone is reacted with a reducing agent known in the art to reduce ketones to alcohols and then alkanes, such as $NaBH—AlCl_3$, borane, and the like. The protecting group is removed to afford the ketone VIB. VIB is reacted with a succinic acid derivative, such as methyl succinate, in the presence of base under Michael-like addition reaction conditions to form the product VIC, which in the presence of base and heat decarboxylates to produce VID. VID is esterfied with alcohol, such as MeOH in acid and the product thereof is reacted with methyl oxalate in base to form the product VIE in situ under Claisen-like condensation reaction conditions, which in base such as NaH, cyclizes under Dieckman condensation reaction conditions to form the product VIF. This is in turn decarboxylates in acid and heat to form VIG. In the presence of HCO—COOnBu and base under Claisen condensation reaction as described in the preparation of compound III, product VIH is formed. This in turn is reacted with dimethylamine under nucleophilic conditions to form the product Compound VII is prepared as follows, 2-cyclohexen-1-one is reacted with ethylene glycol in the presence of acid, such as putoluenesulfonic acid (TSOH) under conditions to form a Ketal protected cyclohexene (VIIB) as described in the article by Laronte, et al. in *Synthetic Communications*, 21(7), 881-884 (1991). It is to be noted that protection of VII A was accompanied by deconjunction of the double bond (isomerism) to form VIIB. Oxidation of VIIB using strong oxidizing agents, such as peracids, e.g., meta-chloro perbenzoic acid (MCPBA) produced the epoxide (VIIC). Reaction of the epoxide with dimethylamine in mineral acid, such as hydrochloric acids, sulfuric acid and the like, produced the amino alcohols VIID and VIIE. Separation of VIID from VIIE is effected using separation techniques known in the art, such as chromatography, e.g., HPLC chromatography, column chromatography and the like. VIID is oxidized by an oxidizing agent known in art such as acid dichromate, $KMnO_4$, $Br_2$, $MnO_2$, ruthenium tetroxide, chromic acid and sulfuric acid in water, $PyrSO_3$, wherein Pyr is pyridine, and the like, to form VIIF. Removal of the ketal protecting groups affords VIIG, which is in equilibrium with the enol form VII.

Compound VIII can be prepared by art recognized techniques as follows:

500 (2000)) and the resulting product is reacted with triisopropylsilicon chloride in the presence of base, such as diisopropylethylamine (Hunigs base) to provide a compound of formula VIIIC. Compound VIIIC is reacted with acid, such as p-toluenesulfonic acid, to afford the product VIIID, where TIPS is triisopropylsilyl (See, e.g., *Journal of Org. Chem.,* 66(11) 3653-3661 (2001), the contents of which are incorporated by reference). VIIID is reacted with dimethylamine in the presence of a reducing agent which reduces the resulting imine to produce the amine of Formula VIIIE. The amine is reacted with tetrabutylammonium fluoride followed by oxidation with PhSeCl and peroxide to form the product of Formula VIIIF (See, *Synthesis* 9, 850-853 (1987) and *Tetrahedron Lett.,* 32(42), 5953-5956 (1991)). The ester is hydrolyzed with acid and then reacted with $NH_3$ under amide forming conditions to afford the product VIII.

Alternatively, the compound of the Formula VIII is formed as follows:

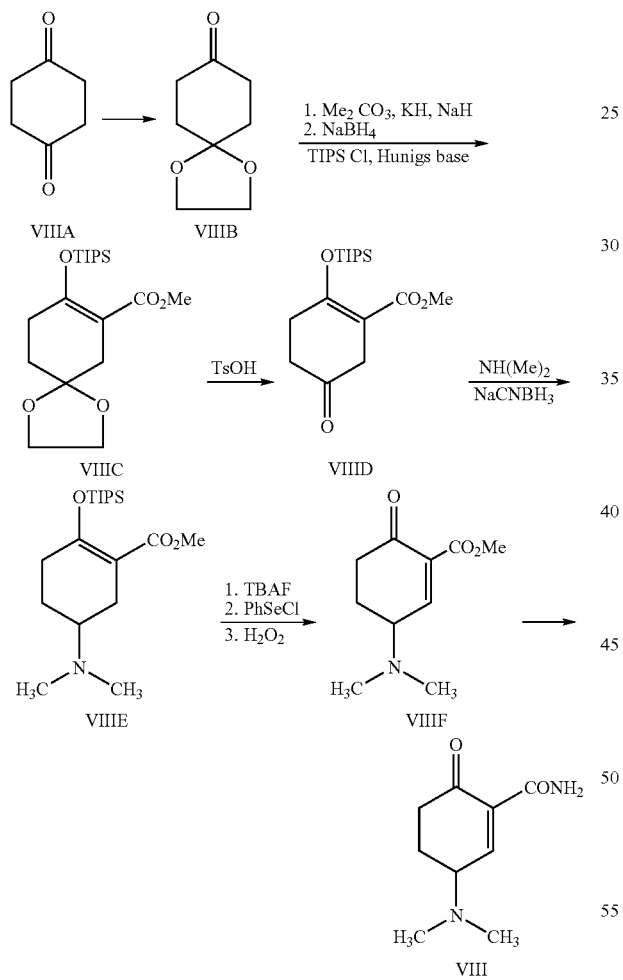

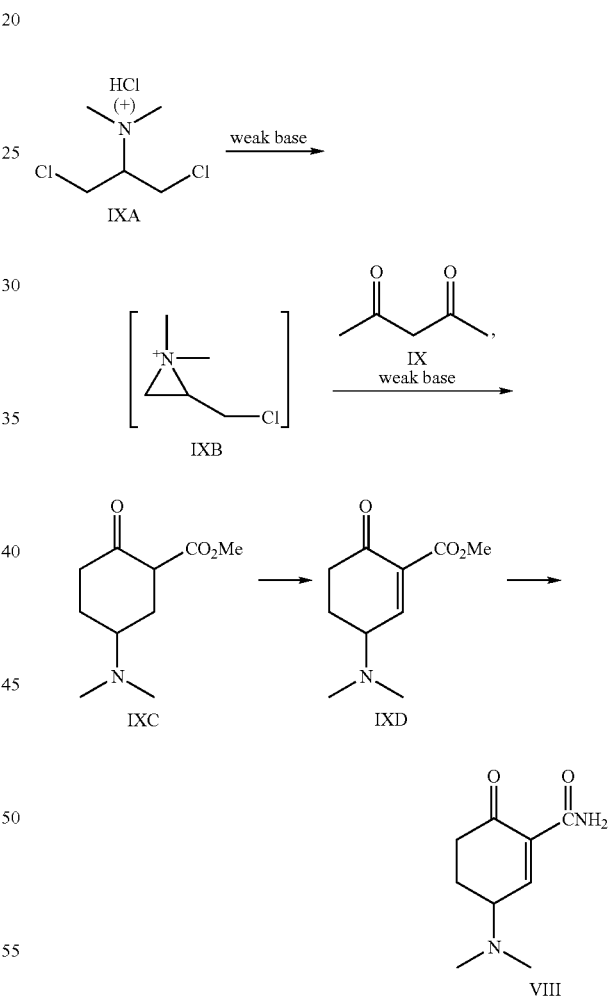

Protection of 1,4-cyclohexadione (VIIIA) with ethylene glycol provides the protected keto ketal (VIIIB). The ketal VIIIB is reacted with methyl carbonate and strong base, such as potassium hydride under Claisen condensation reaction conditions, such as in the preparation of compound III, described hereinabove (See *Synthesis,* 1249-54, (1994). The product thereof is reduced with a reducing agent, such as sodium borohydride, $H_2$/Pt and the like, (See *Synlett,* 4, 497-

IXA is subjected to conditions to form the nitronium, IXB. More specifically, IXA is reacted with a weak organic base, such as tertiary amine, e.g., a salt of diisopropylethylamine salt, in the presence of an inert solvent, such as methylene chloride under conditions effective to form the aziridinium ion, e.g., at temperatures ranging from about 0° C. to the reflux temperature of the solvent, but preferably at about 0° C. The aziridinium ion IXB, which is formed in-situ is reacted with IX in the presence of a weak base such as a tertiary amine under conditions sufficient to form IXC. IXC is converted to IXD as described in Scheme VIII by reacting IXC with a reducing agent such as Na BH$_4$ and then with TIPSCl followed by reacting the product thus formed with an acid such as TsOH; the product thereof is reacted with tetrabutylammonium fluoride followed by oxidation with PhSeCl and peroxide to form the product IXD. The ester in IXD is hydrolyzed in acid and then reacted with NH$_3$ under amide forming conditions to afford the product VIII: which is converted to VIII as described in Scheme VIII.

The compounds of the present invention are effective in lowering the excess IgE concentrations in the plasma. However, they do not suffer from the disadvantages described hereinabove associated with the tetracyclines, minocycline or doxycyclines. Moreover, since the compounds of Formulae I-VIII are smaller molecules, they have a higher bioavailability than the corresponding tetracyclines and thus higher amounts of these molecules can be absorbed into the blood and plasma than the corresponding tetracyclines. Thus, significantly less drug is required to be administered relative to the tetracyclines for efficacy.

While the foregoing specification teaches the principle of the present invention, with examples provided for the purposes of illustration, these teachings will make apparent to those skilled in the art other embodiments and examples. These other embodiments and examples are also within the scope of the present invention.

What is claimed is:

1. A compound having the formula

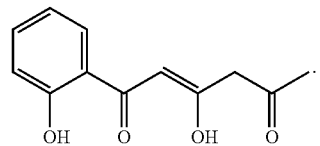

2. A pharmaceutical composition comprising a pharmaceutically effective amount of a compound of claim 1 and a pharmaceutical carrier therefor.

3. A method of lowering the IgE concentration in the plasma of a mammal having a higher then normal concentration of IgE in its plasma comprising administering thereto a therapeutically effective amount of a compound of claim 1.

4. A method of treating a subject suffering from a disease or condition selected from a group consisting of allergy or inflammatory condition or asthma—has been characterized by excess IgE concentration in the plasma of said subject comprising administering to said subject a therapeutically effective amount of a compound of claim 1.

5. The method according to claim 4 wherein the subject matter is a mammal.

6. The method according to claim 4 wherein the mammal is a human.

* * * * *